United States Patent [19]

Patchett et al.

[11] Patent Number: 5,122,511
[45] Date of Patent: Jun. 16, 1992

[54] IMMUNOSUPPRESSIVE CYCLOSPORIN ANALOGS WITH MODIFIED AMINO ACIDS AT POSITION-8

[75] Inventors: Arthur A. Patchett, Westfield; David Taub, Metuchen; Robert T. Goegelman, Linden, all of N.J.

[73] Assignee: Merck & Co., Inc., Rahway, N.J.

[21] Appl. No.: 485,920

[22] Filed: Feb. 27, 1990

[51] Int. Cl.⁵ .................. C07K 5/12; C07K 7/64; A61K 37/00
[52] U.S. Cl. .................. 514/11; 530/317; 530/321
[58] Field of Search .................. 514/11; 530/317, 321

[56] References Cited

U.S. PATENT DOCUMENTS

| | | |
|---|---|---|
| 298,516 | 1/1990 | Durette et al. . |
| 4,102,877 | 7/1978 | Nutt . |
| 4,108,985 | 8/1978 | Rüegger et al. ............ 530/321 |
| 4,117,118 | 9/1978 | Harri et al. . |
| 4,210,581 | 7/1980 | Rüegger et al. ............ 530/321 |
| 4,220,641 | 9/1980 | Traber et al. . |
| 4,288,431 | 9/1981 | Traber et al. . |
| 4,289,851 | 9/1981 | Traber et al. . |
| 4,384,996 | 5/1983 | Bollinger et al. . |
| 4,396,542 | 8/1983 | Wenger . |
| 4,639,434 | 1/1987 | Wenger et al. ............ 514/11 |
| 4,681,754 | 7/1987 | Siegl . |
| 4,703,033 | 10/1987 | Seebach ............ 514/11 |
| 4,764,503 | 8/1988 | Wenger ............ 514/11 |
| 4,798,823 | 1/1989 | Witzel ............ 514/11 |
| 4,914,188 | 4/1990 | Durette et al. . |

FOREIGN PATENT DOCUMENTS

| | | |
|---|---|---|
| 0056782 | 7/1982 | European Pat. Off. . |
| 0194972 | 9/1986 | European Pat. Off. . |
| 0296122 | 12/1988 | European Pat. Off. . |
| 002206119 | 12/1988 | Fed. Rep. of Germany . |
| 2206119 | 12/1988 | United Kingdom . |

OTHER PUBLICATIONS

Traber et al., Chemical Abstracts, 1988, BA 88(5): 48607.
H. Kobel and R. Traber, Directed Biosynthesis of Cyclosporins, European J. Appln. Microbiol Biotechnol., 14, 237–240 (1982).
J. Kollonitsch, Isr. J. Chem., 17, 53–59, 1978.
R. Wenger, Cyclosporine vol. I. pp. 14–25 (1983).
R. Wenger, Total Synthesis—Change in Molecular Structure—Biological Effect: Cyclosporin as Example, Sandorama, 1984/111, pp. 4–11.
R. M. Wenger, Synthesis of Cyclosporine and Analogues: Structural Requirements for Immunosuppressive Activity, Angewandte Chemic 24:2, 77–138 (Feb. 1985).
P. L. Durette et al., A Study of the Correlation Between Cyclophilin Binding and In Vitro Immunosuppressive Activity of Cyclosporine A and Analogues, Transplantation Proceedings, vol. X, No. 2, Suppl. 2 (Apr.), 1988; pp. 51–57.

Primary Examiner—Lester L. Lee
Assistant Examiner—A. M. Davenport
Attorney, Agent, or Firm—Curtis C. Panzer; Hesna J. Pfeiffer

[57] ABSTRACT

New immunosuppressive cyclosporin analogs are disclosed consisting of [dehydro-Ala]⁸ cyclosporins and derived therefrom cyclosporins having a sulfur containing amino acid at position-8.

11 Claims, No Drawings

IMMUNOSUPPRESSIVE CYCLOSPORIN ANALOGS WITH MODIFIED AMINO ACIDS AT POSITION-8

BACKGROUND OF THE INVENTION

The cyclosporins are a family of, neutral, hydrophobic cyclic undecapeptides, containing a novel nine-carbon amino acid (MeBmt) at position 1 of the ring that exhibit potent immunosuppressive, antiparasitic, fungicidal, and chronic anti-inflammatory properties. The naturally occuring members of this family of structurally related compounds are produced by various fungi imperfecti. Cyclosporins A and C, are the major components. Cyclosporin A, which is discussed further below, is a particularly important member of the cyclosporin family of compounds. Twenty four minor metabolites, also oligopeptides, have been identified: Lawen et al, J. Antibiotics 42, 1283 (1989); Traber et al, Helv. Chim. Acta 70, 13 (1987); Von Wartburg and Traber Prog. Med. Chem., 25, 1 (1988).

Isolation of cyclosporins A and C, as well as the structure of A were reported by A. Ruegger et al., Helv. Chim. Acta 59, 1075(1976); M. Dreyfuss et al., J. Appl. Microbiol. 3, 125 (1976). Crystal and molecular structures of the iodo derivative of A have been reported by T. J. Petcher et al., Helv. Chim. Acta 59, 1480 (1976). The Structure of C was reported by R. Traber et al., ibid. 60, 1247 (1977). Production of A and C has been reported by E. Harri et al., U.S. Pat. No. 4,117,118 (1978 to Sandoz). Isolation, characterization and antifungal activity of B, D, E, as well as the structures of A through D have been reported by R. Traber et al., Helv. Chim. Acta 60, 1568(1977). Isolation and structures of E, F, G, H, I: eidem, ibid. 65, 1655 (1982). Preparation of [2-Deutero-3-fluoro-D-Ala]$^8$-CsA is disclosed by Patchett et al in GB 2,206,199A which was published on Dec. 29, 1988.

Further properties have also been reported in studies of the biological activity of A: J. F. Borel et al., Agents Actions 6, 468 (1976). Pharmacology: eidem, Immunology 32, 1017 (1977); R. Y. Calne, Clin. Exp. Immunol. 35, 1 (1979). Human studies: R. Y. Calne et al., Lancet 2, 1323(1978); R. L. Powles et al., ibid. 1327; R. L. Powles et al., ibid 1, 327 (1980). In vitro activity (porcine T-cells): D. J. White et al., Transplantation 27, 55 (1979). Effects on human lymphoid and myeloid cells: M. Y. Gordon, J. W. Singer, Nature 279, 433(1979). Clinical study of A in graft-versus-host disease: P. J. Tutschka et al., Blood 61, 318(1983).

As exemplified by the ever expanding list of indications for which Cyclosporin A has been found useful, the cyclosporin family of compounds find utility in the prevention of rejection or organ and bone marrow transplants; and in the treatment of psoriasis, and a number of autoimmune disorders such as type 1 diabetes mellitus, multiple sclerosis, autoimmune uveitis, and rheumatoid arthritis. Additional indications are discussed infra.

As is generally accepted by those of skill in the art, inhibition of secretion of interleukin-2 (IL-2) and other lymphokines from lymphocytes, is a useful indicator of intrinsic immunosuppressive activity of a cyclosporin analog. For a recent review of cyclosporin uses and mechanisms of action see Wenger et al Cyclosporine: Chemistry, Structure-Activity Relationships and Mode of Action, Progress in Clinical Biochemistry and Medicine, vol. 2, 176 (1986).

Cyclosporin A is a cyclic peptide which contains several N-methyl amino acids and, at position-8, contains a D-alanine.

Structure of Cyclosporin A$^a$

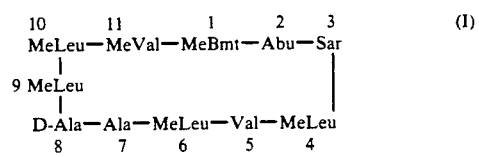

(I)

Abu = L-αAminobutyric acid
Ala = L-Alanine
MeBmt = N-Methyl-(4R)-4-[(E)-2-butenyl]-4-methyl-L-threonine
Leu = L-Leucine
MeLeu = N-Methyl-L-leucine
MeVal = N-Methyl-L-valine
Nva = L-Norvaline
Sar = Sarcosine
Thr = L-Threonine
Val = L-Valine
$^a$Unless otherwise specified, each of the amino acids of the disclosed cyclosporin is of the L-configuration.

A generic structure, useful for describing cyclosprin A and analogs thereof is

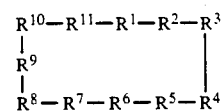

wherein the superscript number defines the position of the amino acid. Because of our specific interest in the amino acid at position 8, we will hereinafter replace "R$^8$" with "Y", thereby emphasizing that amino acid.

As is the practice in the field, a particular cyclosporin analog may be named using a shorthand notation identifying how the analog differs from cyclosporin A. Thus, cyclosporin C which differs from cyclosporin A by the threonine at position-2 may be identified as [Thr]$^2$-cyclosporin or [Thr]$^2$-CsA. Similarly, cyclosporin B is [Ala]$^2$-CsA; cyclosporin D is [Val]$^2$-CsA; cyclosporin E is [Val]$^{11}$-CsA; cyclosporin F is [3-DesoxyMeBmt]$^1$-CsA; cyclosporin G is [NVa]$^2$-CsA; and cyclosporin H is [D-MeVal]$^{11}$-CsA.

D-Serine and D-Threonine have been introduced into the 8-position of cyclosporin A by biosynthesis resulting in active compounds. See R. Traber et al. J. Antibiotics 42, 591 (1989). D-Chloroalanine has also been introduced into position-8 of Cyclosporin A by biosynthesis. See A. Lawen et al J. Antibiotics 52, 1283 (1989).

The present invention concerns new analogs of cyclosporin A and related cyclosporins for the care of immunoregulatory disorders and diseases, including the prevention, control and treatment thereof.

SUMMARY OF THE INVENTION

This invention relates to [dehydro-Ala]$^8$ cyclosporins and their preparation and conversion to novel cyclosporin analogs useful as alternatives to cyclosporin A. More specifically, the invention relates to [dehydro-Ala]$^8$ cyclosporins and derived therefrom cyclosporin analogs having a sulfur containing amino acid at position-8.

DETAILED DESCRIPTION OF THE INVENTION

This invention relates to cyclosporin analogs of the formula

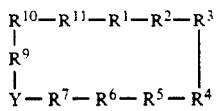

wherein the amino acid moiety at position-8 is Y, and Y is [dehydro-Ala], namely

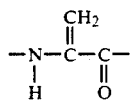

or Michael thio adducts of [dehydro-Ala], namely

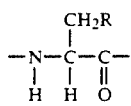

wherein

R is $CH_3(O—CH_2—CH_2)_n—S(O)_m—$, wherein m is 0 or 1 and n is 1,2,3, or 4; or $R_aS(O)_m—$, wherein $R_a$ is selected from the group consisting of
1) H, provided that m is 0;
2) $C_{1-6}$ alkyl, such as methyl, ethyl, isopropyl or tert-butyl;
3) substituted $C_{1-6}$ alkyl wherein the substitutent is selected from the group consisting of,
   (a)

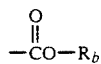

wherein $R_b$ is $C_{1-6}$ alkyl or hydrogen,
   (b) $—NR_bR_c$ wherein $R_c$ is $C_{1-6}$ alkyl or hydrogen;
   (c) $C_{1-6}$ acylamino-;
   (d) -hydroxy; and
   (e) $C_{1-6}$ acyloxy-;
4) benzyl or phenyl;
5) substituted benzyl or phenyl wherein substitutents are selected from the group consisting of $C_{1-4}$ alkyl, hydroxyl, $C_{1-4}$ alkyloxy, and halo,
6)

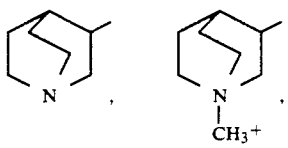

wherein
$R^1$ may be, but is not limited to MeBmt, 3-desoxyMeBmt or dihydroMeBmt;
$R^2$ may be, but is not limited to Abu, Ala, Nva, SeR, Thr or Val;
$R^3$ may be, but is not limited to, Sar or N-methyl-D-alanyl;
$R^4$ may be, but is not limited to MeLeu or MeVal;
$R^5$ may be, but is not limited to Val or Nva;
$R^6$ may be, but is not limited to, MeLeu or MeVal;
$R^7$ may be, but is not limited to Ala, Abu, or L-phenylalanyl;
$R^9$ may be, but is not limited to MeLeu or MeVal;
$R^{10}$ may be, but is not limited to MeLeu, or MeVal; and
$R^{11}$ may be, but is not limited to MeVal, D-MeVal or MeNva.

One embodiment within the scope of the invention, is the cyclosporin analogs selected from the group consisting of:
(a) [3-DesoxyMeBmt]$^1$[Y]$^8$-CsA;
(b) [Ala]$^2$[Y]$^8$-CsA;
(c) [Thr]$^2$[Y]$^8$-CsA and dihydro [Thr]$^2$[Y]$^8$-CsA;
(d) [Val]$^2$[Y]$^8$-CsA and dihydro [Val]$^2$[Y]$^8$-CsA;
(e) [Nva]$^2$[Y]$^8$-CsA and dihydro and iso [Nva]$^2$[Y]$^8$-CsA;
(f) [D-MeVal]$^{11}$[Y]$^8$-CsA; and
(g) [Val]$^{11}$[Y]$^8$-CsA.

One class of compounds within the embodiment is the compounds wherein, R is $CH_3(OCH_2CH_2)_n—S(O)_m$ wherein m is 0 or 1 and n is 1,2,3 or 4 or $R_aS(O)m$; m is 0 is 1; and $R_a$ is selected from the group consisting of
1) H unless m is 1,
2) $C_{1-6}$ alkyl, such as methyl, ethyl, isopropyl or tert-butyl;
3) substituted $C_{1-6}$ alkyl wherein the substitutent is selected from the group consisting of,
   (a)

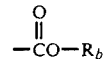

wherein $R_b$ is $C_{1-6}$ alkyl or hydrogen,
   (b) $C_{1-6}$ acylamino-,
   (c) $—NR_bR_c$ wherein $R_c$ is $C_{1-6}$ alkyl or hydrogen;
   (d) -hydroxy; and
   (e) $C_{1-6}$ acyloxy-.

A second embodiment within the scope of the invention, is the compounds of formula II

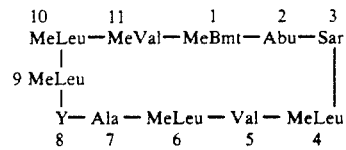

One class of compounds within this embodiment is the compounds wherein, R is $CH_3(OCH_2CH_2)_n—S(O)_m$ wherein m is 0 or 1 and n is 1,2,3 or 4 or $R_aS(O)m$; wherein m is 0 or 1; and $R_a$ is selected from the group consisting of
1) H provided that m is 0,
2) $C_{1-6}$ alkyl, such as methyl, ethyl, isopropyl or tert-butyl;
3) substituted $C_{1-6}$ alkyl wherein the substitutent is selected from the group consisting of,
   (a)

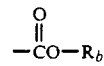

wherein $R_b$ is $C_{1-6}$ alkyl or hydrogen,
   (b) $C_{1-6}$ acylamino-, (c) —$NR_bR_c$ wherein $R_c$ is $C_{1-6}$ alkyl or hydrogen;
(d) -hydroxy; and
(e) $C_{1-6}$ acyloxy-.

Illustrating this class are:
D-[3-methylthio-Ala]$^8$-CsA;
D-[3-carbomethoxymethylthio-Ala]$^8$-CsA;
D-[3(2-hydroxyethylthio)Ala]$^8$-CsA; [dehydro-Ala]$^8$-CsA;
D-[3-benzylthio-Ala]$^8$-CsA;
D-[3-phenylthio-Ala]$^8$-CsA;
D-[3-methylthio-Ala]$^8$-CsA sulfoxide;
D-[3-(2-hydroxyethylthio)Ala]$^8$-CsA sulfoxide; and
D-[methoxyethoxy)ethoxyethylthio-Ala]$^8$-CsA.

Compounds of the present invention are conveniently prepared using the procedures described generally below and more explicitly in the Example Section thereafter.

Now turning to Scheme 1, in one embodiment the cyclosporin analogs of this invention are conveniently prepared via conversion of [X-D-Ala]$^8$-CsA to [Δ-Ala]$^8$-CsA.

Scheme 1

[X-D-Ala]$^8$-CsA $\xrightarrow{\text{LDA/THF}}$ [ΔAla]$^8$-CsA

[Δ-Ala]$^8$-CsA $\xrightarrow{R_aSH}$ [$R_a$S-Ala]$^8$-CsA wherein X is fluoro, chloro, methanesulfonyloxy, toluenesulfonyloxy and $R_a$ is the broadest definition of $R_a$ provided above.

According to Scheme 1 [2-deutero-3-fluoro-D-Ala]$^8$-CsA (abbreviated as [F-D-Ala]$^8$-CsA), in an aprotic solvent, is reacted with an aprotic base to yield [ΔAla]$^8$-CsA.

[F-D-Ala]$^8$-CsA possesses 17 active hydrogens (12-αCH, 4-NH AND 1-OH). Accordingly, a large excess of aprotic base is required to generate the polyanion. The molar ratio of aprotic base to [F-D-Ala]$^8$-CsA may range from 17 to 35 of which 20-25 is preferred. Suitable aprotic bases include, but are not limited to, mono or di$C_{1-6}$alkylamido derivatives such as lithium diethylamide, lithium diisopropylamide, sodium bis (trimethylsilyl)amide, lithium bis (trimethylsilyl)amide of which lithium diisopropylamide is preferred. Suitable aprotic solvents include, but are not limited to, di$C_{1-4}$alkoxy $C_{1-4}$alkane derivatives such as 1,2-dimethoxyethane; ethers such as diethyl ether di-n-butyl and diisopentyl ethers, cyclic ethers such as tetrahydropyran, dihydropyran, tetrahydrofurfuryl methyl ether, furan, tetrahydrofuran and 2-ethoxytetrahydrofuran, and mono or di$C_{1-4}$alkyl carbonyl amines such as dimethylformamide. Tetrahydrofuran is preferred.

The reaction may be conveniently conducted in a temperature range of $-100°$ to $-10°$ C., of which $-70°$ to $-30°$ C. is preferred. The reaction is allowed to proceed to completion in 1 to 24 hours, of which a 4 to 5 hour reaction time is preferred.

The [Δ-Ala]$^8$-CsA product can be isolated by standard chromatography, HPCL or TLC on silica gel plates as is known in the art.

[Δ-Ala]$^8$-CsA is then converted into the thio compound [$R^a$S-Ala]-CsA by reaction in a second solvent with a sulfur nucleophile in the presence of a second base.

The second base includes, but is not limited to, the alkali metal $C_{1-6}$alkoxides and hydrides, such as sodium, lithium or potassium methoxide or hydride, of which sodium methoxide is preferred.

The second solvent includes, but is not limited to $C_{1-8}$alkanols corresponding to the selected second base, such as methanol and ethers (as defined above) such as 1,2-dimethoxyethane, or tetrahydrofuran, of which methanol and tetrahydrofuran are preferred. One example of corresponding second solvent and base is methanol and sodium methoxide.

The sulfur nucleophile includes, but is not limited to RSH wherein R is $CH_3(O-CH_2-CH_2)_n-S(O)_m$, and $R_aSH$ wherein $R_a$ is given its broadest definition provided above.

The reaction can be conveniently conducted in a temperature range of 0° to 50° C., of which 15° to 30° C. is preferred. The reaction is allowed to proceed to completion in 1 to 36 hours, of which 15 to 18 hours is preferred.

In Scheme 1 the Δ-Ala moiety of [Δ-Ala]$^8$-CsA serves as a Michael acceptor to various nucleophiles.

As an alternative to the above, [Δ-Ala]-CsA can be produced from [D-Ser]$^8$-CsA. In this procedure [D-Ser]$^8$-CsA is treated with a slight excess of methanesulfonyl chloride or toluenesulfonyl chloride in methylene chloride in the presence of 4-dimethylaminopyridine to yield, after chromatography, [methane or toluene substituted sulfonyloxy-D-Ser]$^8$-CsA. These compounds can be treated with excess LDA in THF at low temperatures to yield [Δ-Ala]$^8$-CsA. Similarly [D-Chloro-Ala]$^8$-CsA can be treated with excess LDA in THF at low temperatures to yield [Δ-Ala]$^8$-CsA.

Compounds [D-RS-Ala]$^8$-CsA (wherein R is $CH_3(O-CH_2-CH_2)n-S(O)m$) and [D-$R_a$S-Ala]$^8$-CsA may also be produced by an alternate route from [D-Cys]$^8$-CsA (which is the same as [D-HS-Ala]$^8$CsA) by reaction with RX and $R_aX$ (wherein $R_a$ is not phenyl or substituted phenyl and X is chlorine, bromine or a sulfonyloxy aryl or alkyl group such as mesyloxy or tosyloxy) as indicated in Scheme 2 which also shows production of [D-HS-Ala]$^8$-CsA by reaction of [Δ-Ala]$^8$-CsA with the sodium salt of thiolacetic acid followed by hydrolysis.

As appreciated by those of skill in the art, the remaining compounds within the scope of the invention can be produced in an analogous manner.

The $SR_a$ groups in the disclosed compounds can be oxidized to the corresponding sulfoxides. A convenient route to sulfoxides is by periodate oxidation as described below.

Scheme 2

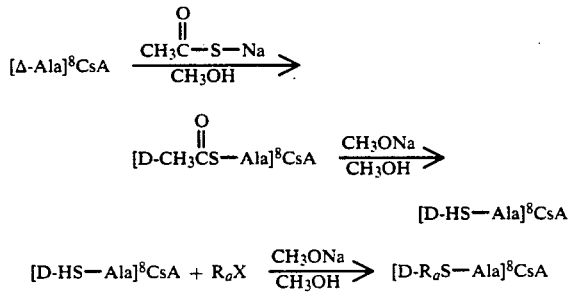

As shown in Scheme 2 treatment of [Δ-Ala]$^8$CsA with 5-10 equivalents of $CH_3COS-Na$ (generated in situ from equivalent quantities of $CH_3COSH$ and $CH_3ONa$) in $CH_3OH$ for 15-18 hr at 20-25° C. produces [D-CH₃COS-Ala]⁸-CsA which is partly deacetylated. Deacetylation to [D-HS-ala]⁸CsA is completed by reaction with CH₃ONa (1-5 equivalents) in a C₁-₈alkanol such as methanol for 3-18 hr at 20-25° C. Reaction of [D-HS-Ala]⁸-CsA with R¹X (5-10 equivalents) in the presence of CH₃ONa (1-2 equivalents) in an C₁-₈alkanol such as CH₃OH for 15-18 hr at 20-25° C. yields [D R$_a$S-Ala]⁸CsA. In this procedure R$_a$ is not phenyl or substituted phenyl.

For example a compound accessible by this route is [D-3-thia-Lys]⁸-CsA, ([D-H₂NCH₂CH₂S-Ala]⁸-CsA). This compound is useful in preparing affinity chromatography columns for cyclosporin receptor isolation and to prepare cyclosporin antibodies.) [D-3-Thia-Lys]⁸CsA may be prepared as indicated in Scheme 3.

Scheme 3

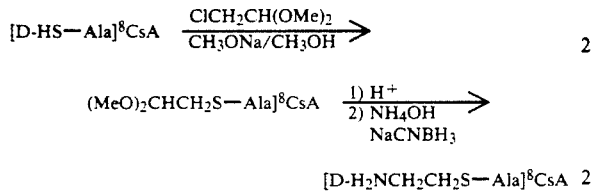

Scheme 4

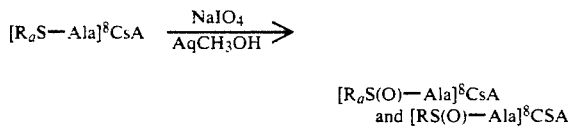

As shown in Scheme 4, the [R$_a$S-Ala]⁸ cyclosporins are converted into the corresponding sulfoxides by treatment with sodium periodate in aqueous alcohol with methanol-water in the ratio 3:1 as the preferred solvent. The time may range from 3 to 36 hours with 15-18 hours preferred. The preferred temperature range is 20-25° C.

In view of their immunosuppressive activity, end product cyclosporins e.g. of formula II, are useful for the prophylaxis and treatment of diseases and conditions requiring a reduction of the immune response. Thus they may be used to suppress the proliferation of lymphocytes and immunocytes, e.g. in treatment of autoimmune diseases or in preventing the rejection of transplants e.g. skin, lung, heart, heart-lung, bone-marrow, kidney, spleen and corneal transplants.

Specific auto-immune diseases for which the cyclosporins of formula II are useful include all of those for which treatment with cyclosporine has been proposed or used, for example, aplastic anaemia, pure red cell anaemia, idopathic thrombocytopaenia, systemic lupus erythematodes, polychondritis, sclerodoma, Wegener granulomatosis, chronic active hepatitis, myasthenia gravis, psoriasis, Steven-Johnson syndrome, idiopathic sprue, Crohn's diseases, Graves opthalmopathy, sarcoidosis, multiple sclerosis, primary biliary cirrhosis, primary juvenile diabetes, uveitis posterior, interstital lung fibrosis and psoriatic arthritis as well as insulin-dependent diabetes mellitus, nephrotic, syndrome and AIDS.

For all these uses the dosage will, of course, vary depending on the compound employed, mode of administration and treatment desired. However, in general, satisfactory results are obtained when administered at a daily dosage of from about 1 mg to about 200 mg per kg animal body weight, conveniently given in divided doses 2 to 4 times a day or in sustained release form. For the larger mammals, the total daily dosage is in the range from about 50 to about 5000 mg. and dosage forms suitable for oral administration comprise from about 15 mg to about 500 mg (e.g. 25-300 mg) of the compounds admixed with a solid or liquid pharmaceutical carrier or diluent.

The present invention also provides a pharmaceutical composition comprising a compound of formula II in association with a pharmaceutical carrier or diluent.

Such compositions may be in the form of, for example, a solution, a tablet or a capsule and in ointments especially for the treatment of psoriasis.

The cyclosporins of formula II may be administered by any conventional route, in particular in accordance with means currently practiced in relation to administration of cyclosporine, in particular via intravenous infusion, e.g. in the case or organ transplant, pre- and immediately post-transplant, as well as during episodes of gastrointestinal disturbance which might otherwise impair absorption, or orally, e.g. in the form of an oral solution.

Biological activity can be measured in terms of binding affinity for cyclophilin, the cytosolic receptor for cyclosporin (R. Handschumacher et al., Science, 226 (1984) 544), inhibition of interleukin-2 production, and inhibition of T-cell proliferation. Table 2 illustrates the pharmacological activity of representative compounds of the present invention.

T-cell proliferation was measured in mouse T-cell cultures stimulated with ionomycin plus phorbol myristate acetate (PMA). Spleen cell suspensions from C57B1/6 mice were prepared and separated on nylon wool columns. The recovered T-cells were suspended at 10⁶ cells/ml in complete culture medium with addition of ionomycin (250 ng/ml) and PMA (10 ng/ml). The cell suspension was immediately distributed in 96 well-flat bottom microculture plates at 100 μl/well. Control medium or various concentrations of test compound were added in triplicate wells at 10 μl/well. The plates were incubated at 37° C. in a humidified atmosphere of 5% CO₂-95% air for 44 hours. At 44 hours of culture, the plates received 20 μl/well of a solution of (3-(4,5-dimethylthiazol-2-yl)-2,5-diphenyltetrazolium bromide (MMT) in PBS (10 mg/ml). To dissolve the purple crystals of MTT formazan produced by metabolically active cells, 100 μl of a 10% SDS-0.01 N hydrochloric acid solution was added to each well. The culture plates were incubated at 37° C. in a 5% CO₂ incubator. The plates were read at 570-600 nm in a multiwell scanning spectrophotometer. The absorbance (specific OD) of experimental wells was corrected for that of wells with unstimulated cells or no cells. The percent inhibition of proliferation was calculated according to the formula:

$$\% \text{ Inhib.} = 100 - \frac{\text{Specific } OD \text{ experimental}}{\text{Specific } OD \text{ control medium}} \times 100$$

TABLE 2

IMMUNOSUPPRESSIVE ACTIVITIES OF CYCLOSPORIN ANALOGS

```
MeLeu—MeVal—MeBmt—Abu—Sar
 |                        |
 MeLeu                    |
 |                        |
 Y——Ala—MeLeu——Val——MeLeu
```

| Y | Cyclophilin Binding[a,b] | T-Cell Proliferation Inhibition[b] |
|---|---|---|
| [CH$_3$S—Ala] | 76. | 53. |
|  |  | 117. |
| [CH$_3$O—C(=O)—CH$_2$—S—Ala] |  | 24. |
|  |  | 33. |
|  |  | 41. |
|  |  | 30. |
| [HOCH$_2$CH$_2$—S—Ala] |  | 50. |
|  |  | 80. |
|  |  | 85. |
|  |  | 54. |
| [Dehydro-Ala] |  | approx. 30. |

[a]This assay is desscribed in detail by R. Handschumacher et al., Science, 226 (1984) 544.
[b]The data are expressed as % CsA activity (CsA(cyclosporin A) = 100).

The following examples illustrate the preparation of the invention compounds of formula II and as such are not to be considered as limiting the invention set forth in the claims appended thereto.

Preparation of the cyclosporin analogs of the instant invention are depicted in Schemes 1–4 above.

Preparation of [2-deutero-3-fluoro D-Ala]$^8$-CsA is disclosed in GB 2,206,119A filed by Patchett et al in Jun. 20, 1988. Preparation [2-deutero-3-fluoro-D-ala]$^8$-CsA is also disclosed in Example 1.

Preparation of fluorinated amino acids such as 3 fluoro-alanine, is well known to those skilled in the art. See, for example, Kollonitsch, J. Israel J. of Chemistry Vol. 17 pp 53–59 (1978) and Durette et al., Transplantation Proceedings Vol 20 No. 2 suppl 2 pp 51–77 (April 1988).

As described above, each of the cyclosporin analogs within the scope of the invention is prepared from a preferred cyclosporin analog starting material possessing [2-deutero-3-fluoro-D-Ala]$^8$ or [3-chloro-D-Ala]$^8$ or [D-Ser]$^8$. These substituted cyclosporin analogs can also be made by total synthesis as taught by Wenger in U.S. Pat. No. 4,396,542 issued Aug. 2, 1983 as amplified in U.S. Pat. No. 4,798,823 issued Jan. 17, 1989, which patents are hereby incorporated by reference. In these total syntheses the D-Ala component is replaced by 2-deutero-3-fluoro-D-Ala, 3-chloro-D-Ala or D-Ser to generate the corresponding 8-substituted cyclosporin.

The remaining starting materials for the process are available commercially, and/or their method of preparation known.

EXAMPLE 1

Preparation of [2-deutero-3-fluoro-D-alanine]$^8$ cyclosporin A

| Culture: Tolypocladium inflatum MF5080, NRRL-8044 | |
|---|---|
|  | g/L |
| Media: Slant Medium A |  |
| Malt Ext. | 20.0 |
| Yeast Ext. | 4.0 |
| Agar | 20.0 |
| Seed Medium B |  |
| Malt Ext. | 70.0 |
| Glucose | 50.0 |
| Culture Medium C |  |
| Glucose | 40.0 |
| Caseinpeptone | 10.0 |
| MgSO$_4$.7H$_2$O | 0.5 |
| KH$_2$PO$_4$ | 2.0 |
| NaNO$_3$ | 3.0 |
| KCl | 0.5 |
| FeSO$_4$.7H$_2$O | 0.01 |

A lyophile tube was aseptically opened and grown in seed medium B (20 ml in a 250 ml 3-baffle Erlenmeyer flask) for 4 days on a rotary shaker (220 rpm) at 27° C.

This seed was then used to inoculate slants (medium A) for future studies. The slants were incubated at 27° C. for 14 days after which time they were stored at 4° C. until used.

The spores were washed from an entire slant with 5 ml of medium C and used to inoculate a preculture flask (50 ml medium C in a 250 ml Erlenmeyer flask). This preculture was incubated for 5 days at 27° C.

Five ml of the preculture was used to inoculate the production medium (50 ml of medium C and 5 mg/ml of 2-deutero-3-fluoro-D-alanine in a 250 ml Erlenmeyer flask). The filter sterilized 2-deutero-3-fluoro-D-alanine was added (5 mg/ml, final concentration) post-sterilization and prior to inoculation. Forty-four flasks containing a total of 2.2 liters of production medium were incubated 14 to 21 days with agitation (220 rpm) at 27° C. Following incubation, the fermentation broths were extracted by procedures described below in item C.

EXAMPLE 2

Preparation of [3-fluoro-D-alanine]$^8$-CsA

Following essentially the same procedures as described in Example 1 except that the preculture was used to inoculate a production medium of a total volumn of 400 ml containing 5 mg/ml of 3-fluoro-D-alanine instead of 2-deutero-3-fluoro-D-alanine, there was obtained the fermentation broth which was extracted by the procedures described below in item C.

A. Extraction Methodology a. The cells were removed from the broth by centrifugation.
b. The clarified broth was extracted 3 times each with 25 ml portions of methylene chloride.
c. The cells were extracted 3 times each with 25 ml portions of acetone.
d. The methylene chloride and acetone extracts were pooled and taken to dryness under vacuum.
e. The residue was solubilized with methanol, dried with anhydrous Na$_2$SO$_4$, filtered and taken to dryness under vacuum.
f. The samples were submitted for HPLC analysis to determine and isolate the cyclosporin derivatives.

B. HPLC Analysis of [F-D-Ala]$^8$ CsA

Crude extracts were assayed by HPLC chromatography using the following chromatographic system.
Solvent: 80/20 v:v acetonitrile:water
Flow rate: 0.6 mL/min Column: DuPont Zorbax ODS 4.6 mm×25 cm maintained at 60° C.
Detector: LDC Spectromonitor III, 210 nm 0.05 AUFS
Integrator: Spectra-Physics SP4100 Computing Integrator The extraction residue from one 400 ml fermentation was taken up in 1 ml of methylene chloride and the solution chromatographed on a 40 ml column of Pharmacia LH-20 previously equilibriated with methanol. The chromatography was carried out with methanol at a flow rate of 2 ml/min., collecting one ten ml fraction followed by 30×1 ml fractions. Fractions 16 through 27 were selected and combined, based on HPLC analysis. The combined fractions were concentrated to dryness and the residue labeled F.

Sample F was taken up in 250 ml of methanol and subjected to preparative HPLC chromatography on a DuPont Zorbax ODS column 0.9×25 cm maintained at 60° C., Chromatography was carried out with a solvent system of 80:20 v:v acetonitrile:water at a flow rate of 2 ml/min. The effuent stream was monitored at 220 nm using an LDC Spectromonitor II equipped with a 1 mm path length cell and a setting 1.28 AUFS. The ultra-violet signal was monitored using a Spectra-Physics SP4100 computing integrator and eleven fractions were collected based on the ultra-violet trace. Fraction 7 contained 3.25 mg of 8-[3-fluoro-D-alanine]$^8$-CsA with an ultra-violet purity of >99% at 210 nm by HPLC analysis. Fraction 7 was concentrated to dryness under high vacuum to yield 3.3 mg of [3-fluoro-D-alanine]$^8$-CsA.

EXAMPLE 3

[Dehydro-Ala]$^8$-CsA

To 2.0 ml of tetrahydrofuran stirred at −78° under nitrogen is added 0.6 ml of 1.5M (0.9 mmol) lithium diisopropylamide in cyclohexane. To this solution is added 50 mg (0.042 mmol) of [2-deutero-3-fluoro D-Ala]$^8$ cyclosporin A in 1.0 ml of tetrahydrofuran. The mixture is stirred at −78° for 30 minutes and the temperature is slowly raised to −30° over 4 hours. The mixture is cooled to −78° and quenched by adding 0.15 ml of acetic acid in 0.9 ml of water. It is then added to 20 ml of saturated aqueous sodium chloride containing 0.2 g of sodium bisulfate and extracted with ethyl acetate (3×20 ml). The latter extract is washed with saturated aqueous sodium chloride (2×20 ml), dried over sodium sulfate and taken to dryness under vacuum. The residue (47 mg) is purified by preparative TLC (three 500 v 20×20 cm silica gel plates; system-chloroform:ethanol=96:4: two developments) to give two major bands. From the more polar band is obtained [dehydro-Ala]$^8$-CsA (17 mg) as a colorless solid; 34% direct yield; 53% conversion yield. HPLC-Dupont Zorbax ODS column; 80:20=CH$_3$CN:H$_2$O/60°; R$_t$=14 minutes. FAB-MS=M+ +1=1200-consistent with molecular formula C$_{62}$H$_{109}$N$_{11}$O$_{12}$.

$^{13}$C NMR Chemical Shifts (CDCl$_3$, 100 MHz): 9.9, 15.8, 16.6, 17.9, 18.6, 18.9, 19.5, 20.2, 21.2, 21.8, 22.0, 23.1, 23.4, 23.7(2×), 23.9, 24.6, 24.7, 24.9, 25.0, 25.2, 29.0, 30.1, 30.4, 31.1, 31.2, 31.3, 32.5, 33.9, 35.6, 35.9, 36.0, 37.1, 39.2, 39.3, 40.8, 48.9, 49.2, 49.3, 50.2, 54.9, 55.2, 55.5, 57.5, 57.8, 58.3, 74.7, 108.3, 126.3, 129.5, 134.8, 167.6, 170.0 170.1, 170.3, 170.5, 170.8, 171.1, 171.9, 173.4, 173.50 and 173.53 ppm. The carbon count of 62 is consistent with the molecular formula. From the less polar band is obtained 19 mg of recovered [2-deutero-3-fluoro-D-Ala]$^8$CsA.

EXAMPLE 4

D-[3-Methylthio-Ala]$^8$-CsA

To a stirred solution of [dehydro-Ala]$^8$ CsA (45 mg; 0.037 mMol) in methanol (1.0 ml) is added sodium methylmercaptide (60 mg) in methanol (1.5 ml). The mixture is kept 18 hours at 20° C. It is then added to 20 ml of saturated aqueous sodium chloride containing 0.3 g sodium bisulfate and the mixture is extracted with ethyl acetate (4×15 ml). The organic extract is washed with saturated aqueous sodium chloride (2×15 ml), dried over sodium sulfate and concentrated to dryness under sodium sulfate and concentrated to dryness under vacuum. The residue (38 mg) is purified by HPLC (column::Dupont Zorbax ODS 0.94×25 cm; solvent system-:acetonitrile:water=70:30; 2.65 ml/min. at 60° C.) to give 12 mg (26%) of D-[3-methylthio-Ala]$^8$ CsA (estimated amount present 16 mg (34%); R$_t$ 20.5 min (CsA=17.4 min) FAB-MS: M+ +1=1248 -consistent with molecular formula C$_{63}$H$_{113}$N$_{11}$O$_{12}$S.

$^{13}$C NMR Chemical Shifts (CDCl$_3$, 75 MHz): 9.8, 15.8, 16.6, 17.0, 17.9, 18.4, 18.8, 19.9, 20.3, 21.2, 21.7, 22.2, 23.3, 23.5, 23.7, 23.81, 23.84, 24.4, 24.6, 24.89, 24.94, 25.4, 29.2, 29.85, 29.93, 30.0, 31.1, 31.3, 31.5, 33.7, 35.4, 35.8, 36.0, 37.1, 37.3, 39.5(2×), 40.6, 48.2, 48.7, 48.8(2×), 50.3, 55.1, 55.36, 55.44, 57.5, 58.1, 58.8, 74.5, 126.3, 129.7, 170.05, 170.07, 170.2, 170.3, 171.1, 171.5, 171.7, 171.9, 173.4, 173.61 and 173.66 ppm. The carbon count of 63 is consistent with the molecular formula.

EXAMPLE 5

D-[3-carbomethoxymethylthio-Ala]$^8$CsA

A solution of methyl mercaptoacetate (25 mg, 0.24 mmol) in methanol (0.5 ml) is added to sodium methoxide (13 mg, 0.24 mmol) and the mixture is added to a solution of [dehydro-Ala]$^8$C$_s$A (11 mg, 0.01 mol) in methanol (0.5 ml). The reaction mixture is kept 18 hours at 20°. It is then worked up as in Example 4 to give 15 mg of crude product which is purified by HPLC (column:Dupont Zorbax ODS; solvent system: methanol:-water=85:15; 2.56 ml/min at 60°) R$_t$=16.9 min (C$_s$A=18.0 min. FAB-MS-M+ +1=1306-consistent with molecular formula C$_{65}$H$_{115}$N$_{11}$O$_{14}$S.

EXAMPLE 6

D-[3(2-Hydroxyethylthio)Ala]$^8$CsA

A solution of 2-mercaptoethanol (21 mg; 0.27 mmol) in tetrahydrofuran (0.5 ml) is added to sodium methoxide (10 mg; 0.18 mmol). To the stirred mixture is added [dehydro-Ala]$^8$ CsA (18 mg; 0.015 mmol) in tetrahydrofuran (0.8 ml). After 18 hours at 20° the reaction mixture is added to ethyl acetate (20 ml). The latter solution is extracted with saturated aqueous sodium chloride (3×15 ml), dried over sodium sulfate and concentrated to dryness under vacuum to give 26 mg of crude product which is purified by HPCL (Column:Dupont Zorbax ODS 0.94×25 cm; solvent system: acetonitrile:-water=75:25, 2.65 ml/min at 60°) R$_t$32 11.5 min (CsA=19.8 min) FAB-MS-M+ +1=1278-consistent with molecular formula C$_{64}$H$_{115}$N$_{11}$O$_{13}$S.

$^{13}$C NMR Chemical Shifts (C$_6$D$_6$, 75 MHz: 10.1, 16.0, 17.8, 18.1, 18.5, 18.8, 20.0, 20.1, 21.4, 21.9, 22.3, 23.6, 23.6, 23.8, 24.2, 24.5, 25.8, 25.2, 25.3, 25.5, 25.8, 29.5, 29.7, 30.0, 30.4, 30.8, 31.6, 31.6, 33.8, 34.9, 35.6, 35.9, 36.5, 36.5, 37.8, 39.0, 39.9, 41.5, 48.9, 49.0, 49.2, 49.5, 50.0, 55.5, 55.6, 55.7, 57.8, 58.3, 59.4, 62.1, 74.5, 126.3, 130.7, 169.6, 170.1, 170.3, 170.4, 171.2, 171.6, 172.2, 172.3, 173.8, 174.1 and 174.3 ppm. The carbon count of 64 is consistent with the molecular formula.

EXAMPLE 7

D-[3(2-Dimethylaminoethylthio)Ala]$^8$CsA

2-Dimethylaminoethylthiol hydrochloride (2 g) is dissolved in 1.5M sodium hydroxide (10 ml) and the mixture extracted with ethyl acetate. The latter extract is dried over sodium sulfate and concentrated to dryness under vacuum to give not dimethylaminoethylthiol but rather the corresponding disulfide, bisdimethylaminoethyl disulfide as a colorless oil. To the latter (32 mg; 0.15 mmol) is added dithiothreitol (22 mg; 0.14 mmol) in methanol (0.5 ml) and the mixture added to sodium methoxide (12 mg; 0.22 mmol). The reagent mixture is stirred under nitrogen for 20 minutes and then [dehydroAla]$^8$C$_s$A (17 mg; 0.014 mmol) in methanol (0.8 ml) is added. The reaction mixture is kept under nitrogen for 18 hours and worked up as in Example 4. The crude product (45 mg) is purified by HPLC. FAB-MS-M$^+$+1=1305-consistent with molecular formula C$_{66}$H$_{120}$N$_{12}$O$_{12}$S.

EXAMPLE 8

D-[3(2-Hydroxyethylthio)-Ala]$^8$ CsA Sulfoxide

To a stirred solution of D-[3(2-hydroxyethylthio)Ala]$^8$CsA (35 mg) in methanol (2 ml) is added a solution of NaIO$_4$ (15 mg) in water (0.6 ml). The reaction mixture is stirred at room temperature for 18 hr. The formed precipitate of NaIO$_3$ is removed by filtration and washed with methanol. The combined filtrate and washings are concentrated under vacuum to a small volume. Ethyl acetate is added. The organic phase is washed with saturated aqueous NaCl, dried over Na$_2$SO$_4$ and concentrated to dryness. The residue is purified is purified by HPLC: FAB-MS-M$^+$+1=1294-consistent with molecular formula C$_{64}$H$_{115}$N$_{11}$O$_{14}$S.

What is claimed is:

1. A compound of the formula

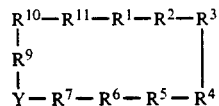

wherein Y is selected from the group consisting of
(a) [dehydro-Ala],

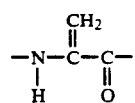

and,
(b) thio adducts of [dehydro-Ala] of the formula

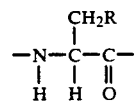

wherein R is CH$_3$(O—CH$_2$—CH$_2$)$_n$—S(O)$_m$—, wherein m is 0 or 1 and n is 1,2,3, or 4; or R$_a$S(O)$_m$, and R$_a$ is selected from the group consisting of
1) H provided m is 0;
2) C$_{1-6}$ alkyl;
3) substituted C$_{1-6}$ alkyl wherein the substitutent is selected from the group consisting of,
(a)

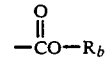

wherein R$_b$ is C$_{1-6}$ alkyl or hydrogen,
(b) C$_{1-6}$ acylamino-,
(c) —NR$_b$R$_c$ wherein R$_c$ is C$_{1-6}$ alkyl or hydrogen;
(d) -hydroxy; and
(e) C$_{1-6}$ acyloxy-;
4) benzyl or phenyl;
5 substituted benzyl or phenyl wherein substitutents are selected from the group consisting of C$_{1-4}$ alkyl, hydroxyl, C$_{1-4}$ alkyloxy, and halo; and

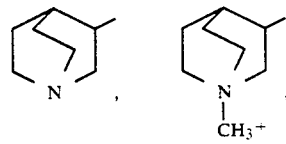

wherein
R$^1$ is MeBmt, 3-desoxyMeBmt or dihydroMeBmt;
R$^2$ is Abu, Ala, Nva, Ser, Thr or Val;
R$^3$ is Sar or N-methyl-D-alanyl;
R$^4$ is MeLeu or MeVal;
R$^5$ is Val or Nva;
R$^6$ is MeLeu or MeVal;
R$^7$ is Ala, Abu, or L-phenyl-alanyl;
R$^9$ is to MeLeu or MeVal;
R$^{10}$ is MeLeu, or MeVal; and
R$^{11}$ is MeVal, D-MeVal or MeNva.

2. A compound according to claim 1 selected from the group consisting of
(a) [3-DesoxyMeBmt]$^1$[Y]$^8$-CsA;
(b) [Ala]$^2$[Y]$^8$-CsA;
(c) [Thr]$^2$[Y]$^8$-CsA and dihydro [Thr]$^2$[Y]$^8$-CsA;
(d) [Val]$^2$[Y]$^8$-CsA and dihydro [Val]$^2$[Y]$^8$-CsA;
(e) [Nva]$^2$[Y]$^8$-CsA and dihydro and iso [Nva]$^2$[Y]$^8$-CsA;
(f) [D-MeVal]$^{11}$[Y]$^8$-CsA; and
(g) [Val]$^{11}$[Y]$^8$-CsA.

3. A compound according to claim 2 wherein R is CH$_3$(OCH$_2$CH$_2$)$_n$—S(O)$_m$ wherein m is 0 or 1 and n is 1,2,3 or 4 or R$_a$S(O)m; m is 0 or 1; and R$_a$ is selected from the group consisting of
1) H unless m is 1,
2) C$_{1-6}$ alkyl,
3) substituted C$_{1-6}$ alkyl wherein the substitutent is selected from the group consisting of,
(a)

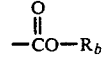

wherein R$_b$ is C$_{1-6}$ alkyl or hydrogen,
(b) C$_{1-6}$ acylamino-, (c) —NR$_b$R$_c$ wherein R$_c$ is C$_{1-6}$ alkyl or hydrogen;
(d) -hydroxy; and
(e) C$_{1-6}$ acyloxy-.

4. A compound according to claim 1 of formula II

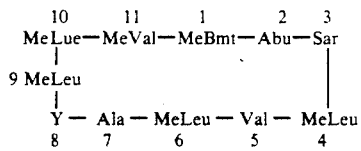

5. A compound according to claim 4 wherein R is CH$_3$(OCH$_2$CH$_2$)$_n$—S(O)$_m$ wherein m is 0 or 1 and n is 1,2,3 or 4 or R$_a$S(O)$_m$ wherein m is 0 or 1 and R$_a$ is selected from the group consisting of
1) H, unless m is 1;
2) C$_{1-6}$ alkyl, such as methyl, ethyl, isopropyl or tert-butyl;
3) substituted C$_{1-6}$ alkyl wherein the substitutent is selected from the group consisting of,
(a)

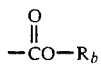

wherein R$_b$ is C$_{1-6}$ alkyl or hydrogen,
(b) —NHR$_b$,
(c) C$_{1-6}$ acylamino-,
(d) —NR$_b$R$_c$ wherein R$_c$ is C$_{1-6}$ alkyl or hydrogen;
(e) -hydroxy; and
(f) C$_{1-6}$ acyloxy-.

6. A compound according to claim 5, selected from the group consisting of
(a) D-[3-methylthio-Ala]$^8$-CsA;
(b) D-[3-carbomethoxymethylthio-Ala]$^8$-CsA;
(c) D-[3(2-hydroxyethylthio)Ala]$^8$-CsA;
(d) D-[dehydro-Ala]$^8$-CsA;
(e) D-[3-benzylthio-Ala]$^8$-CsA;
(f) D-[3-phenylthio-Ala]-CsA;
(g) D-[3-methylthio-Ala]$^8$CsA sulfoxide;
(h) D-[3-(2-hydroxyethylthio)Ala]$^8$CsA sulfoxide; and
(i) D-[(2-methoxyethoxy)ethoxyethylthio-Ala]$^8$-CsA.

7. A pharmaceutical composition for inducing immunosuppression or treating inflammation in a subject in need of such treatment, comprising a therapeutically effective amount of a compound according to claim 1.

8. A pharmaceutical composition for inducing immunosuppression or treating inflammation in a subject in need of such treatment, comprising a therapeutically effective amount of a compound according to claim 4.

9. A pharmaceutical composition for inducing immunosuppression or treating inflammation in a subject in need of such treatment, comprising a therapeutically effective amount of a compound according to claim 6.

10. A method of treating inflamation in a subject in need of such treatment, comprising administering a therapeutically effective amount of compound according to claim 1.

11. A method of inducing immunosuppression in a subject in need of such treatment, comprising administering a therapeutically effective amount of compound according to claim 1.

* * * * *